(12) United States Patent
Zhu et al.

(10) Patent No.: US 9,128,060 B2
(45) Date of Patent: Sep. 8, 2015

(54) RAMAN DETECTING SYSTEM

(71) Applicants: Tsinghua University, Beijing (CN); HON HAI PRECISION INDUSTRY CO., LTD., New Taipei (TW)

(72) Inventors: Zhen-Dong Zhu, Beijing (CN); Qun-Qing Li, Beijing (CN); Ben-Feng Bai, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 14/251,838

(22) Filed: Apr. 14, 2014

(65) Prior Publication Data
US 2015/0204791 A1    Jul. 23, 2015

(30) Foreign Application Priority Data
Jan. 23, 2014    (CN) .......................... 2014 1 00315957

(51) Int. Cl.
*G01J 3/44*     (2006.01)
*G01N 21/65*    (2006.01)
*G01N 21/01*    (2006.01)

(52) U.S. Cl.
CPC .............. *G01N 21/658* (2013.01); *G01N 21/01* (2013.01); *G01N 2201/02* (2013.01)

(58) Field of Classification Search
USPC ............................................... 356/301, 72–73
See application file for complete search history.

(56) References Cited

U.S. PATENT DOCUMENTS

2005/0224779 A1 *  10/2005  Wang et al. ...................... 257/9
2011/0063613 A1 *  3/2011  Sun et al. ......................... 356/301

* cited by examiner

*Primary Examiner* — Abdullahi Nur
(74) *Attorney, Agent, or Firm* — Novak Druce Bove + Quigg LLP

(57) ABSTRACT

A Raman detecting system includes a bowl shaped metal nanostructure array configured to load a sample, a projecting module configured to project a beam of light to the bowl shaped metal nanostructure array, and a receiving module configured to collect the light scattered by the bowl shaped metal nanostructure array. The bowl shaped metal nanostructure array includes a substrate having a surface and a number of particle-in-bowl structures located on the surface of the substrate. Each particle-in-bowl structure includes a bowl shaped concave structure and a protruding member protruding from the bowl shaped concave structure. The protruding member is integrated with the bowl shaped concave structure.

20 Claims, 9 Drawing Sheets

RAMAN DETECTING SYSTEM

RELATED APPLICATIONS

This application claims all benefits accruing under 35 U.S.C. §119 from China Patent Application No. 201410031595.7, filed on Jan. 23, 2014, in the China Intellectual Property Office. This application is related to commonly-assigned application Ser. No. 14/252,079 entitled "METHOD FOR MAKING BOWL SHAPED METAL NANOSTRUTURE ARRAY", concurrently filed; and commonly-assigned application entitled "BOWL SHAPED METAL NANOSTRUTURE ARRAY", concurrently filed. Disclosures of the above-identified applications are incorporated herein by reference.

FIELD

The present application relates to a Raman detecting system.

BACKGROUND

A stable Surface-enhanced Raman Scattering (SERS) substrate with high enhancement is key in a Raman detecting system. A typical SERS substrate is usually composed of rough metal surface or coupled metal particles. The SERS substrate can be fabricated by means of a wet-state process and depositing Ag particles on a multi-walled carbon nanotube (MWCNT)-alumina-coated silica film. However, the method usually leads to some defects and lower sensitivity of the Raman detecting system.

What is needed, therefore, is to provide a Raman detecting system having higher sensitivity.

BRIEF DESCRIPTION OF THE DRAWINGS

Many aspects of the exemplary embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
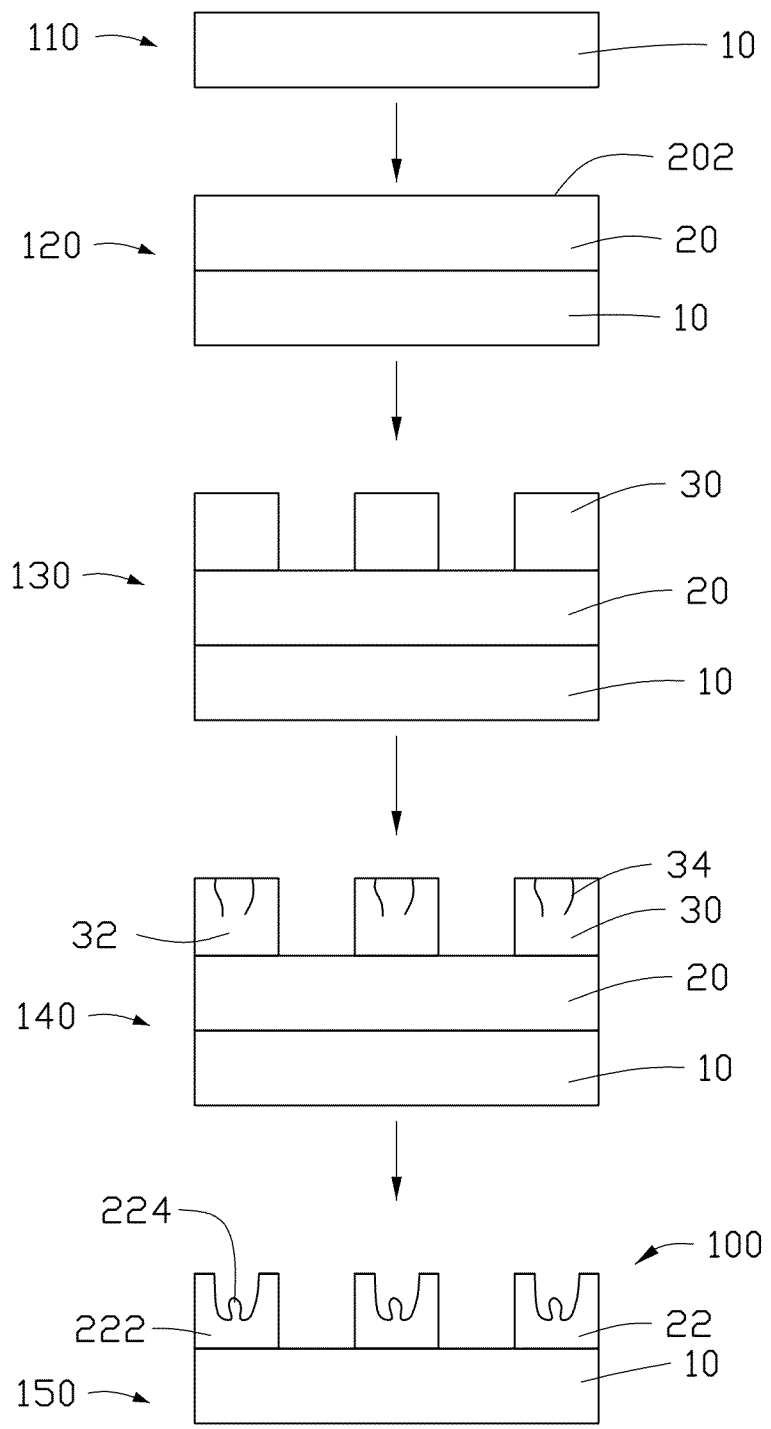
FIG. 1 is a process flow of one embodiment of a method for making bowl shaped metal nanostructure array.
Figure 2:
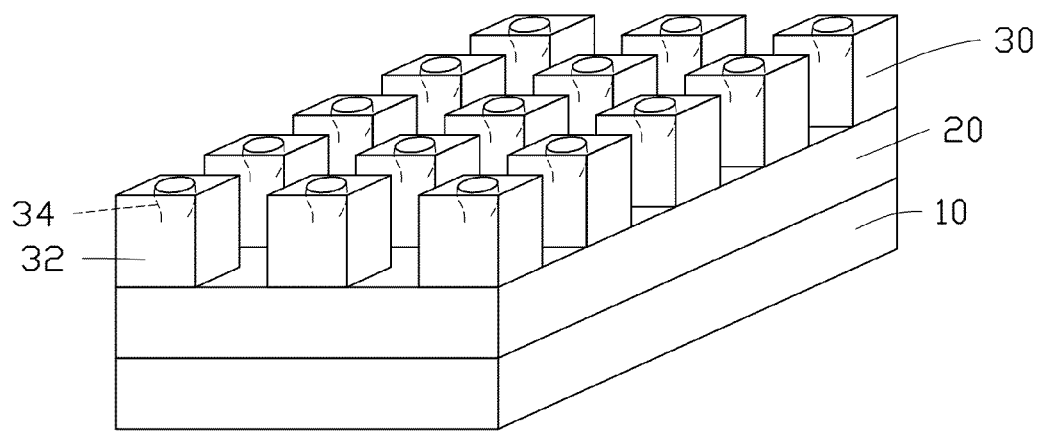
FIG. 2 is a three-dimensional view of flaws of FIG. 1.

Referring to FIGS. 1 and 2, a method for making a bowl shaped metal nanostructure array 100 of one embodiment includes steps of:

providing a substrate 10, in 110;

providing a metal layer 20 on the substrate 10, wherein the metal layer 20 has a top surface 202 away from the substrate 10, in 120;

applying a pattern mask layer 30 on the top surface 202 of the metal layer 20, wherein portion of the top surface 202 of the metal layer 20 is covered by the pattern mask layer 30, in 130;

annealing and forming a plurality of flaws 34 in the pattern mask layer 30, in 140; and etching by physical etching gas and reactive etching gas, to form the bowl shaped metal nanostructure array 100, in 150.

In 110, the substrate 10 can be an insulative substrate or a semiconductor substrate. The substrate 10 can be made of glass, quartz, silicon (Si), silicon dioxide ($SiO_2$), silicon nitride ($Si_3N_4$), gallium nitride (GaN), gallium arsenide (GaAs), aluminum oxide ($Al_2O_3$), or magnesium oxide (MgO). The substrate 10 can also be made of a doped material such as doped N-type GaN or P-type GaN. A size and a thickness of the substrate 10 can be used according to need. In one embodiment, the substrate 10 is a square sapphire substrate with a GaN semiconductor epilayer grown thereon. In at least one embodiment, a side length of the substrate 10 is about 2 centimeters.

In 120, the metal layer 20 can be deposited on a surface of the substrate 10 by a method of electron beam evaporation, chemical vapor deposition (CVD), or sputtering. The thickness of the metal layer 20 can be in a range from about 100 nanometers to about 200 nanometers. The material of the metal layer 20 can be copper, titanium, aluminum or noble metal, such as gold, silver, platinum, or plalladium. In at least one embodiment, the metal layer 20 is made of gold, and the thickness of the metal layer 20 is about 150 nanometers.

In 130, the pattern mask layer 30 includes a plurality of protruding structures 32 substantially parallel with and spaced from each other to form an array. A shape of each of the plurality of protruding structures 32 can be cuboidal, cubic, or cylindrical. In one embodiment, the shape of each of the plurality of protruding structures 32 is cubic. A width of each of the plurality of protruding structures 32 can be in a range from about 80 nanometers to about 300 nanometers. A distance between two adjacent protruding structures 32 can be in a range from about 20 nanometers to about 100 nanometers. A portion of top surface 202 of the metal layer 20 is exposed through the distance between two adjacent protruding structures 32, and the rest of top surface 202 of the metal layer 20 is covered by the plurality of protruding structures 32.

The pattern mask layer 30 can be made by spin-coating a photo resist on the top surface 202 of the metal layer 20 and nano-imprinting the photoresist. The pattern mask layer 30 can be made by etching the photoresist. The photoresist includes ZEP520, Polymethylmethacrylate (PMMA), Polystyrene (PS), PMMA-b-PS, PMMA-t-PS, PS-b-PMMA, or PS-t-PMMA. The thickness of the pattern mask layer 30 can be in a range from about 200 nanometers to about 400 nanometers. In one embodiment, the thickness ratio between the pattern mask layer 30 and the metal layer 20 can be in a range from about 2:1 to about 2.5:1. In at least one embodiment, the pattern mask layer 30 is made of PMMA, and the thickness of the pattern mask layer 30 is about 375 nanometers.

In 140, annealing and forming the plurality of flaws 34 in the pattern mask layer 30 includes steps of:

first, locating a whole structure formed by 130 in an annealing furnace, wherein the whole structure includes the substrate 10, the metal layer 20 located on the substrate 10, and the pattern mask layer 30 located on the top surface 202 of the metal layer 20;

second, introducing an inert gas, such as nitrogen or argon;

third, heating the annealing furnace up to a temperature ranging from about 105° C. to about 180° C. for about 1 minute to about 120 minutes; and fourth, taking the whole structure out of the annealing furnace after cooling the annealing furnace to room temperature.

In 140, in the process of annealing, different positions inside of each protruding structure 32 respond differently to the annealing. There is a stress concentration or phase separation at a position close to top surface of each of the plurality of protruding structures 32. Thus, the position close to top surface of each of the plurality of protruding structures 32 is torn, to form the plurality of flaws 34 in the top surface of each of the plurality of protruding structures 32, as shown in FIG. 2.

In 150, a structure treated by 140 is placed in an etching system filled with physical etching gas and reactive etching gas. The physical etching gas and reactive etching gas can be selected according to the materials of the metal layer 20 and the pattern mask layer 30. The physical etching gas can be argon (Ar) or helium (He). The reactive etching gas can be chlorine ($Cl_2$), boron trichloride ($BCl_3$), oxygen ($O_2$) and carbon tetrafluoride ($CF_4$). In one embodiment, the physical etching gas is Ar, the reactive etching gas is $O_2$.

Figure 3:
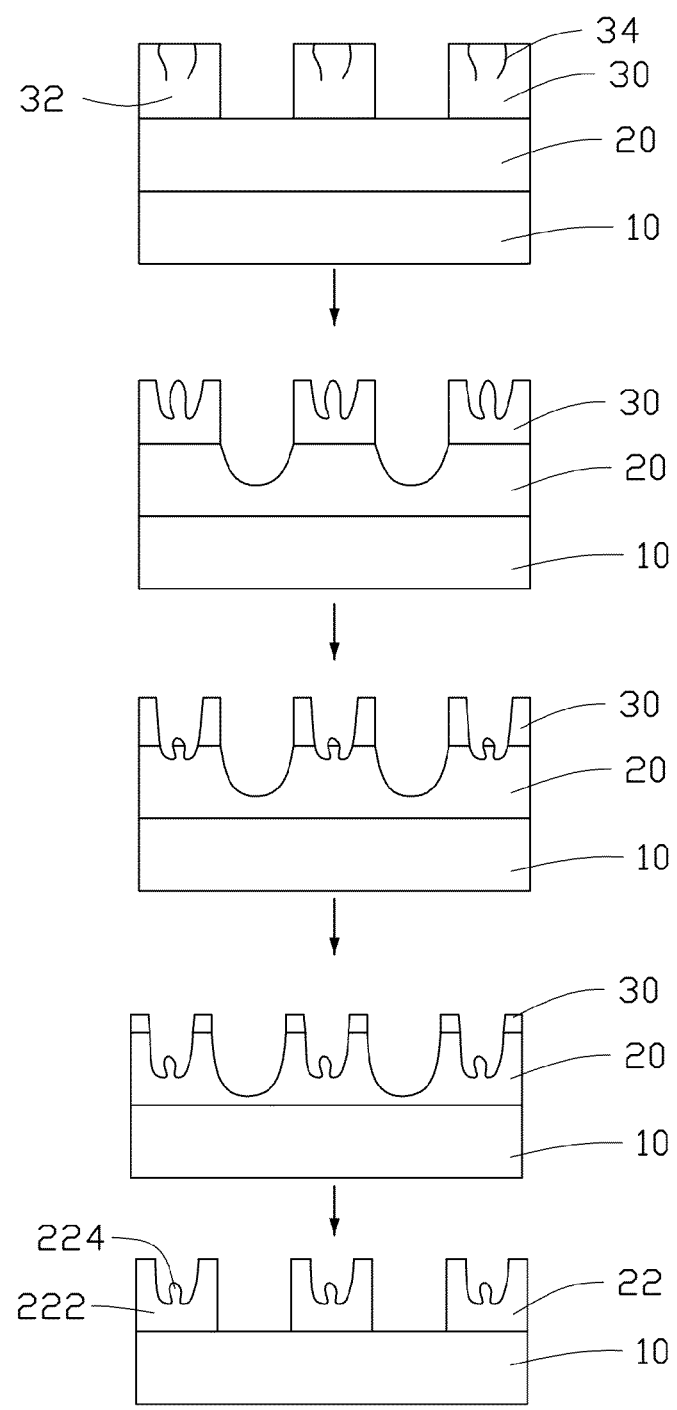
FIG. 3 is a process flow of an etching process of the method of FIG. 1.

Referring to FIG. 3, when the structure treated by 140 is placed in the etching system, the top surface of the plurality of protruding structures 32 is gradually etched by the reactive etching gas. The plurality of flaws 34 is also gradually etched by the reactive etching gas and enlarges, until the metal layer 20 is partially exposed through the plurality of flaws 34. On the other hand, the metal layer 20 exposed through the distance between two adjacent protruding structures 32 is gradually etched by the physical etching gas. And the metal layer 20 exposed through the plurality of flaws 34 is also gradually etched by the physical etching gas.

The pattern mask layer 30 can be totally etched by the reactive etching gas. The metal layer 20 exposed out of the two adjacent protruding structures 32 is totally or partially etched by the physical etching gas. The metal layer 20 exposed through the plurality of flaws 34 is partially etched to form a plurality of bowl shaped concave structures 222 and a protruding member 224 in bottom of each of the plurality of bowl shaped concave structures 222. The protruding member 224 protrudes out of the bottom of each of the plurality of bowl shaped concave structures 222. The protruding member 224 is integrated with each of the plurality of bowl shaped concave structures 222. A bowl shaped metal nanostructure is formed in a position corresponding to each of plurality of protruding structures 32. Thus, the bowl shaped metal nanostructure array 100 including a plurality of bowl shaped metal nanostructures is formed.

Figure 4:
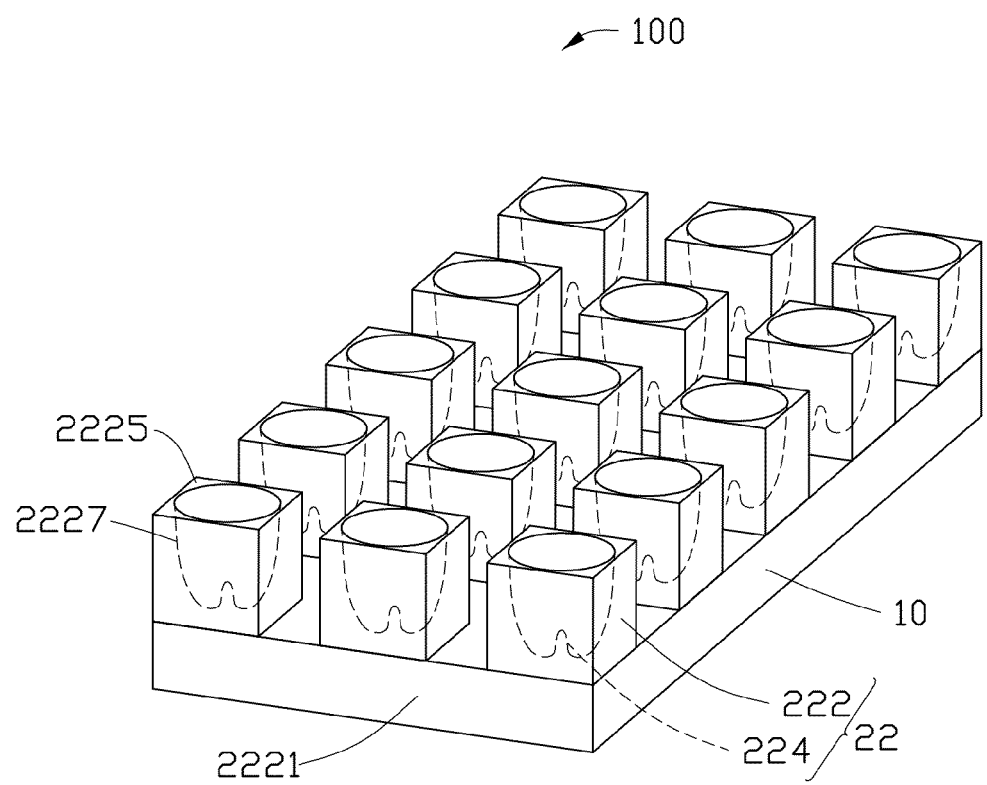
FIG. 4 is a three-dimensional schematic view of the bowl shaped metal nanostructure array.
Figure 5:
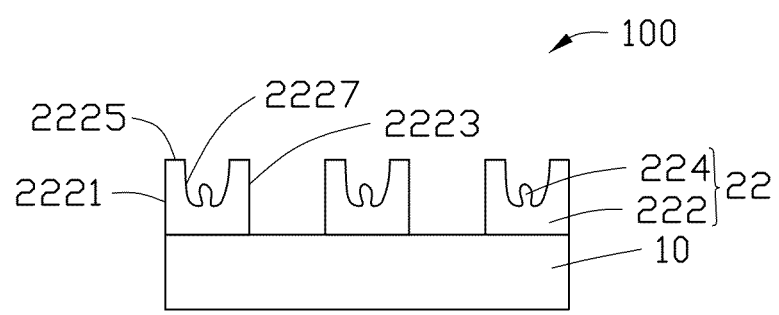
FIG. 5 is a cross-sectional schematic view of FIG. 4.
Figure 6:
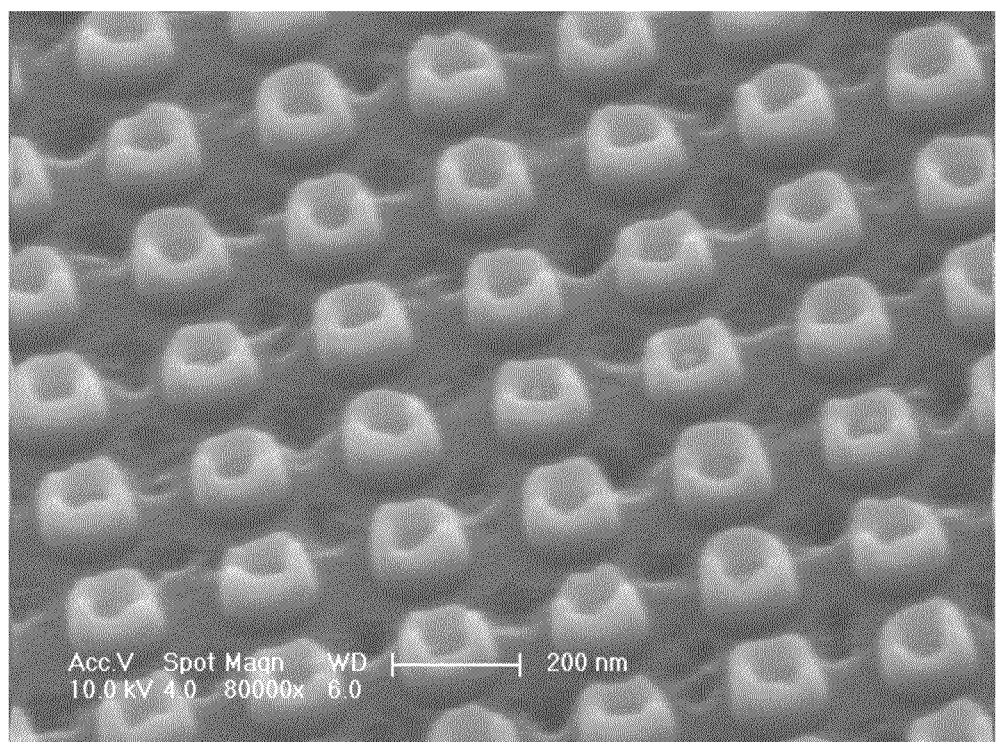
FIG. 6 shows a scanning electron microscope (SEM) image of the bowl shaped metal nanostructure array of FIG. 4.
Figure 7:
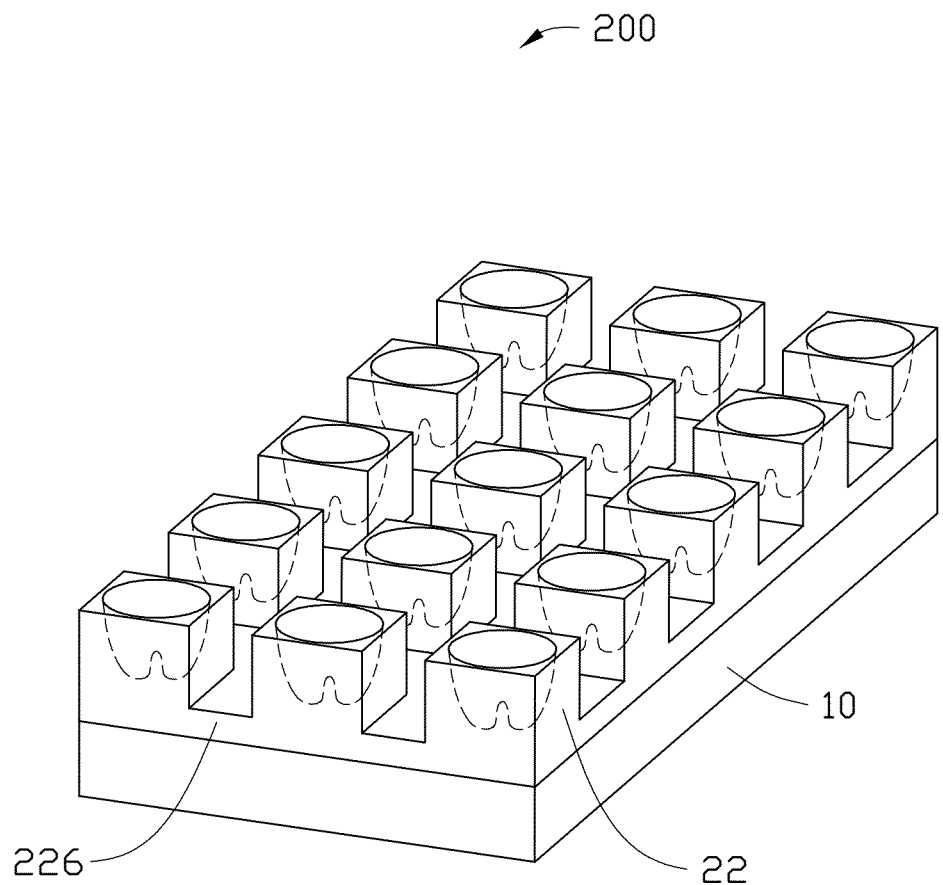
FIG. 7 is a three-dimensional schematic view of another bowl shaped metal nanostructure array.
Figure 8:
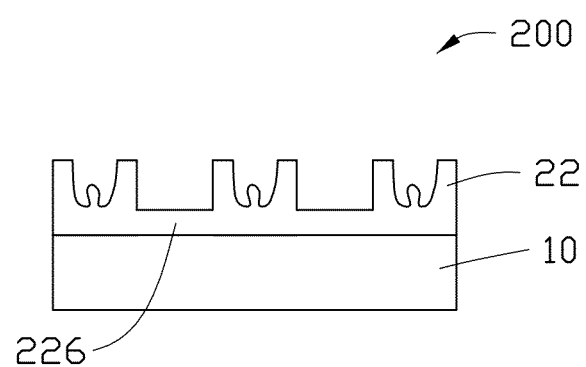
FIG. 8 is a cross-sectional schematic view of FIG. 7.

A flow speed of the physical etching gas can range from about 25 sccm to about 150 sccm, a flow speed of the reactive etching gas can range from about 5 sccm to about 15 sccm. A power of the etching system can be in a range form about 40 watts to about 100 watts. A pressure of the etching system can be in a range from about 10 Pa to about 30 Pa. An etching time can be in a range from about 11 min to about 21 min. When the etching time is in a range from about 16 min to about 21 min, the metal layer 20 exposed through the distance between two adjacent protruding structures 32 is totally etched by the physical etching gas, as shown in FIGS. 4-6. When the etching time is in a range from about 11 min to about 15 min, the metal layer 20 exposed through the distance between two adjacent protruding structures 32 is partially etched by the physical etching gas, as shown in FIGS. 7-8.

Referring to FIGS. 4-8, the bowl shaped metal nanostructure array 100 includes the substrate 10 and a plurality of particle-in-bowl structures 22 located on the substrate 10. Each of the plurality of particle-in-bowl structures 22 includes a bowl shaped concave structure 222 and a protruding member 224 in the bottom of the bowl shaped concave structure 222. Each protruding member 224 is integrated with a bowl shaped concave structure 222. The protruding member 224 and the bowl shaped concave structure 222 are made by the same metal. A shape of the protruding member 224 is arbitrary, such as spherical or cylindrical. In one embodiment, the metal is Au, the shape of the protruding member 224 is spherical, and each of the plurality of particle-in-bowl structures 22 is a particle-in-bowl structure.

Referring to FIG. 5, the bowl shaped concave structure 222 includes a first side surface 2221, a second side surface 2223 opposite to the first side surface 2221, two upper surfaces 2225, and an inside surface 2227. The protruding member 224 is in a middle of the inside surface 2227, and protruded out of the inside surface 2227. The protruding member 224 is integrated with the bowl shaped concave structures 222.

A distance between the upper surface 2225 and the lowest point of the inside surface 2227 can be in a range from about 20 nanometers to about 200 nanometers. A distance between the upper surface 2225 and the top surface of the substrate 10 can be in a range from about 40 nanometers to about 300 nanometers. A distance between the first side surface 2221 and the second side surface 2223 can be in a range from about 100 nanometers to about 850 nanometers. The largest width of the inside surface 2227 can be in a range from about 40 nanometers to about 600 nanometers. A diameter of the spherical protruding member 224 can be in a range from about 2 nanometers to about 60 nanometers. A distance between the first side surface 2221 of a first bowl shaped concave structures 222 and the first side surface 2221 of a second bowl shaped concave structures 222 can be in a range from about 200 nanometers to about 1 micron, wherein the first bowl shaped concave structures 222 is adjacent to the second bowl shaped concave structures 222. A distance between two adjacent particle-in-bowl structures 22 can be in a range from about 100 nanometers to about 150 nanometers.

In one embodiment, the distance between the upper surface 2225 and the lowest point of the inside surface 2227 is 30 nanometers. The distance between the upper surface 2225 and the top surface of the substrate 10 is about 50 nanometers. The distance between the first side surface 2221 and the second side surface 2223 is about 200 nanometers. The largest width of the inside surface 2227 is about 150 nanometers. The diameter of the spherical protruding member 224 is about 10 nanometers. The distance between the first side surface 2221 of the first bowl shaped concave structures 222 and the first side surface 2221 of the second bowl shaped concave structures 222 is about 300 nanometers, wherein the first bowl shaped concave structures 222 is adjacent to the second bowl shaped concave structures 222. The distance between two adjacent particle-in-bowl structures 22 is about 100 nanometers.

As shown in FIGS. 4-6, the plurality of particle-in-bowl structures 22 located on the substrate 10 are substantially parallel with, and spaced from, each other to form an array.

As shown in FIGS. 7-8, a bowl shaped metal nanostructure array 200 includes the substrate 10 and the metal layer 20 located on the substrate 10. The plurality of particle-in-bowl structures 22 is located on the top surface 202 of the metal layer 20. Each of the plurality of particle-in-bowl structures 22 has a bottom. The plurality of particle-in-bowl structures 22 is connected through the bottom of each of the plurality of particle-in-bowl structures 22. A connection between the bottom of a first the plurality of particle-in-bowl structures 22 and the bottom of a second the plurality of particle-in-bowl structures 22 is designed as a connection section 226, wherein the first the plurality of particle-in-bowl structures 22 is adjacent to the second the plurality of particle-in-bowl structures 22. Two adjacent particle-in-bowl structures 22 are connected through the connection section 226. The connection section 226 is made by etching the metal layer 20.

Figure 9:
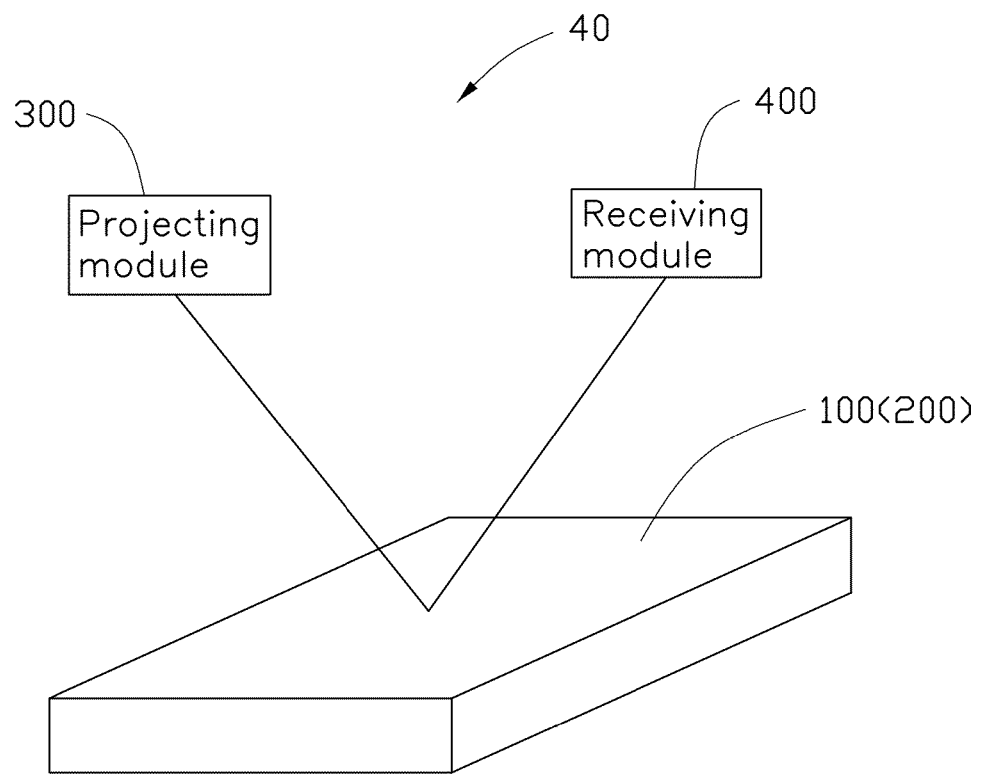
FIG. 9 is a view of a Raman detecting system including the bowl shaped metal nanostructure array of FIG. 1.

Referring to FIG. 9, a Raman detecting system 40 of one embodiment includes a projecting module 300, a surface-enhanced Raman scattering (SERS) substrate, and a receiving module 400. The surface-enhanced Raman scattering (SERS) substrate is the bowl shaped metal nanostructure array 100 or 200.

The bowl shaped metal nanostructure array 100 can be configured to load a sample. Here, the sample is directly contact with the plurality of particle-in-bowl structures 22 of the bowl shaped metal nanostructure array 100. In at least one embodiment, the sample is directly contact with the plurality of protruding members 224 of the plurality of particle-in-bowl structures 22. The sample can be a solid sample or a liquid sample. The solid sample can be sample powders, or particles adhered on the sample thereon. The liquid sample can be drops dissolving the sample therein, or molten sample. In one embodiment, the sample is a water solution of pyridine (volumetric ratio of pyridine to water=1:4).

The projecting module 300 is configured to project a beam of light to the plurality of particle-in-bowl structures 22 to form a scattering light. Area of a cross section of the beam of light on the plurality of particle-in-bowl structures 22 can be less than or equal to 2 square millimeters. The projecting module 300 can include a light source such as argon laser. The light source can have a narrow frequency width. The beam of light can have a wavelength of about 450.0 nanometers to about 514.5 nanometers. In one embodiment, the wavelength of the beam of light is about 514.5 nanometers. More scattering light can be obtained by the beam of light with the wavelength of about 514.5 nanometers.

The receiving module 400 is configured to collect the scattering light scattered by the plurality of protruding members 224 of the plurality of particle-in-bowl structures 22 to form a Raman spectrum figure of the sample adhered on the plurality of protruding members 224. The receiving module 400 can include a multi-channel photon detector such as a charge coupled device (CCD), or a single-channel photon detector such as a photomultiplier. Details of vibrational modes of the sample can be read from the Raman spectrum figure formed by the receiving module 400.

The bowl shaped metal nanostructure array 100 or 200 holding the sample can scatter the beam of light emitted from the projecting module 300, to form the scattering light. The scattering light can report a molecule substructure of the sample.

In detail, when the beam of light is projected to the bowl shaped metal nanostructure array 100 or 200 from the projecting module 300, a diffuse reflection surface will be formed in the plurality of protruding members 224 and the inside surface 2227. The beam of light can collide molecule or functional group of the sample to form the scattering light, wherein the beam of light is diffusely reflected by the diffuse reflection surface. The sample is loaded on the plurality of protruding members 224 or the inside surface 2227 of the plurality of bowl shaped concave structures 222.

The plurality of protruding members 224 are microstructures and can increase electromagnetic field of the inside surface 2227 of the plurality of bowl shaped concave structures 222, further increasing Raman signal. Therefore, the Raman detecting system 40 has higher sensitivity.

The Raman detecting system 40 can be used to detect a message of various molecules. In one embodiment, the Raman detecting system 40 is used to detect a molecule structure of a solution, wherein a concentration of the solution is greater than or equal to $1 \times 10^{-9}$ moles per liter.

In summary, the plurality of particle-in-bowl structures 22 of the bowl shaped metal nanostructure array 100 or 200 is integrated. The plurality of bowl shaped concave structures 222 and the plurality of protruding members 224 have the same metal.

It is to be understood that the above-described embodiment is intended to illustrate rather than limit the disclosure. Variations may be made to the embodiment without departing from the spirit of the disclosure as claimed. The above-described embodiments are intended to illustrate the scope of the disclosure and not restricted to the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. A Raman detecting system, comprising:
a bowl shaped metal nanostructure array configured to load a sample;
a projecting module configured to project a beam of light to the bowl shaped metal nanostructure array; and
a receiving module configured to collect light scattered by the bowl shaped metal nanostructure array;
wherein the bowl shaped metal nanostructure array comprises:
a substrate having a surface; and
a plurality of particle-in-bowl structures located on the surface of the substrate, each of the plurality of particle-in-bowl structures comprises a bowl shaped concave structure and a protruding member protruding from the bowl shaped concave structure, wherein the protruding member is integrated with the bowl shaped concave structure.

2. The Raman detecting system of claim 1, wherein the protruding member and the bowl shaped concave structure are made by the same metal.

3. The Raman detecting system of claim 2, wherein the metal is copper, titanium, aluminum, gold, silver, platinum, or plalladium.

4. The Raman detecting system of claim 1, wherein a shape of the protruding member comprises a spherical portion.

5. The Raman detecting system of claim 4, wherein a diameter of the spherical protruding member is in a range from about 2 nanometers to about 60 nanometers.

6. The Raman detecting system of claim 1, wherein the bowl shaped concave structure comprises an inside surface, the protruding member is in a middle of the inside surface and protruded out of the inside surface.

7. The Raman detecting system of claim 1, wherein the plurality of particle-in-bowl structures is substantially parallel with and spaced from each other to form an array.

8. The Raman detecting system of claim 7, wherein a distance between two adjacent particle-in-bowl structures is in a range from about 100 nanometers to about 150 nanometers.

9. The Raman detecting system of claim 1, wherein the protruding member and the bowl shaped concave structure are made by gold.

10. A Raman detecting system, comprising:
a bowl shaped metal nanostructure array configured to load a sample;
a projecting module configured to project a beam of light to the bowl shaped metal nanostructure array; and
a receiving module configured to collect light scattered by the bowl shaped metal nanostructure array;
wherein the bowl shaped metal nanostructure array comprises:
a substrate;
a metal layer located on the substrate, wherein the metal layer has a surface away from the substrate; and
a plurality of particle-in-bowl structures located on the surface of the metal layer, each of the plurality of particle-in-bowl structures comprises a bowl shaped concave structure and a protruding member protruding from the bowl shaped concave structure, wherein the protruding member is integrated with the bowl shaped concave structure.

11. The Raman detecting system of claim 10, wherein the protruding member and the bowl shaped concave structure are made by the same metal.

12. The Raman detecting system of claim 11, wherein the metal is copper, titanium, aluminum, gold, silver, platinum, or plalladium.

13. The Raman detecting system of claim 10, wherein the protruding member and the bowl shaped concave structure are made by gold.

14. The Raman detecting system of claim 10, wherein the bowl shaped concave structure comprises an inside surface, the protruding member is in a middle of the inside surface and protruded out of the inside surface.

15. The Raman detecting system of claim 10, wherein a shape of the protruding member comprises a spherical.

16. The Raman detecting system of claim 15, wherein a diameter of the spherical protruding member is in a range from about 2 nanometers to about 60 nanometers.

17. The Raman detecting system of claim 10, wherein a thickness of the metal layer between two adjacent particle-in-bowl structures is in a range from about 5 nanometers to about 80 nanometers.

18. A Raman detecting system, comprising:
a bowl shaped metal nanostructure array configured to load a sample;
a projecting module configured to project a beam of light to the bowl shaped metal nanostructure array; and
a receiving module configured to collect light scattered by the bowl shaped metal nanostructure array;
wherein the bowl shaped metal nanostructure array comprises a plurality of particle-in-bowl structures that share a substrate, each of the plurality of particle-in-bowl structures comprises a bowl shaped concave structure and a protruding member protruding from the bowl shaped concave structure, wherein the protruding member and the bowl shaped concave structure are made by the same metal.

19. The Raman detecting system of claim 18, wherein the metal is copper, titanium, aluminum, gold, silver, platinum, or plalladium.

20. The Raman detecting system of claim 18, wherein the bowl shaped concave structure comprises an inside surface, the protruding member is in a middle of the inside surface and protruded out of the inside surface.

* * * * *